(12) United States Patent
Egashira

(10) Patent No.: US 6,703,210 B2  
(45) Date of Patent: Mar. 9, 2004

(54) METHOD AND DEVICE FOR DETERMINING CONCENTRATION OF DIOXINS

(75) Inventor: Naoyoshi Egashira, 103-8,Minami-Hatajiki-Machi, Miyoshi-Shi, Hiroshima-Ken (JP)

(73) Assignees: Satake Corporation, Tokyo (JP); Naoyoshi Egashira, Miyoshi (JP)

( * ) Notice: Subject to any disclaimer, the term of this patent is extended or adjusted under 35 U.S.C. 154(b) by 56 days.

(21) Appl. No.: 09/984,495

(22) Filed: Oct. 30, 2001

(65) Prior Publication Data

US 2002/0052051 A1 May 2, 2002

(30) Foreign Application Priority Data

Nov. 2, 2000 (JP) ........................................ 2000-336122

(51) Int. Cl.[7] ............................................... G01N 33/53
(52) U.S. Cl. ...................... 435/7.93; 435/7.1; 435/7.92; 436/518; 436/524; 436/544; 436/543; 530/388.9
(58) Field of Search ................................. 435/7.1, 7.92, 435/7.93; 436/518, 524, 543, 525, 544, 536, 815, 172; 530/388.9

(56) References Cited

U.S. PATENT DOCUMENTS

| | | | |
|---|---|---|---|
| 4,238,472 A | * | 12/1980 | Albro et al. ................... 424/1 |
| 5,075,447 A | * | 12/1991 | Muller et al. ................. 546/10 |
| 5,128,244 A | * | 7/1992 | Poland et al. ............... 435/7.93 |
| 5,538,852 A | | 7/1996 | Carlson et al. |
| 5,674,697 A | * | 10/1997 | Carlson et al. ............ 435/7.93 |
| 5,830,341 A | | 11/1998 | Gilmartin |
| 6,127,136 A | * | 10/2000 | Wheelock et al. .......... 435/7.94 |
| 6,140,138 A | * | 10/2000 | Bard et al. ................... 435/537 |
| 6,432,722 B1 | * | 8/2002 | Punzmann et al. ......... 436/514 |

FOREIGN PATENT DOCUMENTS

| | | |
|---|---|---|
| JP | 11-79719 | 3/1999 |
| JP | 11-326222 | 11/1999 |
| WO | WO 96/24062 | 8/1996 |

* cited by examiner

*Primary Examiner*—Long V. Le  
*Assistant Examiner*—Gary Counts  
(74) *Attorney, Agent, or Firm*—Oblon, Spivak, McClelland, Maier & Neustadt, P.C.

(57) ABSTRACT

A method for determining the concentration of dioxins present in a sample comprises the steps of chemically linking a hapten having a structure mimic to a part of the structures of dioxins with a ruthenium complex to thus form an antigen; incubating the resulting antigen together with an antibody fixed to or immobilized on an electrode to thus induce an antigen-antibody reaction; oxidizing or reducing the ruthenium complex by applying an electric voltage to the reaction product through the electrode to thus induce electrolytic light emission; and observing the electrolytically emitted light rays to quantitatively determine the amount of the antigen and to thus evaluate the concentration of the dioxins present in the sample. The present invention permits the elimination of the use of any reagent such as hydrogen peroxide required for the chemical luminescence, the highly sensitive analysis of dioxins and the miniaturization of the device to be used in the analysis of dioxins.

6 Claims, 4 Drawing Sheets

METHOD AND DEVICE FOR DETERMINING CONCENTRATION OF DIOXINS

This application claims priority to a Japanese application No. 2000-336122 filed on Nov. 2, 2000.

BACKGROUND OF THE INVENTION

The present invention relates to a method and a device for determining the concentration of dioxins present in a sample. More particularly, the invention relates to a method and a device that permit the highly sensitive and highly selective determination of the concentration of polychlorinated dibenzo-p-dioxins (PCDDs) including virulently poisonous 2,3,7,8-tetrachloro-dibenzo-p-dioxin ($T_4CDD$) and likewise virulently poisonous polychlorinated dibenzofurans (PCDFs), which are generated during the incineration of general waste and industrial waste.

Dioxins are generated in a high concentration when the waste is incinerated and this has recently constituted a serious problem. Accordingly, one has been obligated to control the concentration of dioxins included in the exhaust gas generated during the incineration of the foregoing waste to a level of not higher than 0.1 $ng/Nm^3$ as expressed in terms of the total amount of the dioxins and homologues and isomers thereof as well as the homologues and isomers of polychlorinated dibenzofuran, because the dioxins are virulently poisonous. However; it is needed to detect dioxins present in such a low concentration, which is beyond the detection limit of the usual analysis methods, because of the virulent toxicity of the dioxins and the exhaust gas to be analyzed contains a great variety of impurities and contaminants such as dust and mist in a large quantity. For this reason, the direct and precise determination and/or quantification of dioxins require a complicated pre-treatment of the exhaust gas and the use of a specially designed analysis device.

A typical quantitative analysis method comprises the steps of extracting an exhaust gas with a solvent such as toluene or ethylene glycol for 72 hours using a Soxhlet's extractor, cleaning up the extract, concentrating the extract and then analyzing it using a gas chromatography-mass spectrometer. This method includes the use of complicated steps required for the analysis such as a concentration step. Therefore, it takes two or three weeks till the analysis is completed or desired results are obtained and the analysis is quite expensive.

Japanese Un-Examined Patent Publication (hereunder simply referred to as "J.P. KOKAI") No. Hei 11-326222 proposes an indirect method for quantitatively analyzing dioxins, which can eliminate the use of any operation for concentrating a sample containing dioxins and which employs a relatively cheap device, and this method comprises the steps of mixing a halogen atom-containing organic solvent, metal complexes of 8-oxyquinoline and a sample whose concentration of dioxins is to be determined; irradiating the resulting mixture with excited light rays to determine the intensity of the emitted fluorescent light rays and to thus quantitatively analyze halophenols whose concentration is well correlated with that of the dioxins present in the sample; and estimating the concentration of the dioxins on the basis of the concentration of the halophenols thus determined.

In this method, however, (1) the liquid to be analyzed may interact with the fluorescent complexes and therefore, any influence of components present in the liquid, which may compete with the halophenols, should be examined in advance and (2) the correlation between the concentrations of the halophenols and dioxins should be examined in advance. The results obtained by the method may greatly be influenced by the factors concerning the kinds of dioxins. Accordingly, this method may be a means considerably inferior in the precision since the concentration of the dioxins present in the liquid is indirectly evaluated. In addition, the fluorescent method is highly sensitive, but the method is quite susceptible to coexisting substances and the excited light rays are inevitably incident upon the system for observation (or a detection system) and therefore, the method does not always ensure desired high sensitivity.

Incidentally, J.P. KOKAI No. Hei 11-79719 discloses a method for reversibly absorbing and desorbing a gas without using conventionally used absorbent such as activated carbon and silica gel. This method comprises bringing a pair of electrodes into contact with a solution containing a ruthenium complex capable of absorbing and releasing molecular nitrogen and simultaneously controlling the electric voltage applied to the electrodes to thus absorb and desorb nitrogen gas and therefore, this method permits (1) the control of the absorption and desorption of the gas at ordinary temperature and pressure without application of any heat; (2) the control of the gas absorption and desorption simply by adjusting the electric voltage to be applied to the electrodes; and (3) the reversible and repeated absorption and desorption of the gas. In this method, which makes use of a solution containing a ruthenium complex capable of absorbing and releasing molecular nitrogen, however, there are some problems remaining unsolved, for instance, a problem as to whether, or not, the method permits the absorption and desorption of substances having planar structures such as dioxins and homologues and isomers thereof as well as homologues and isomers of polychlorinated dibenzofuran.

SUMMARY OF THE INVENTION

The inventors of this invention have found that the use of a ruthenium complex permits the highly selective determination of dioxins, while taking into consideration the foregoing problems associated with the conventional techniques. Accordingly, it is an object of the present invention to provide a method and a device for determining the concentration of dioxins present in a sample, which make use of a novel measurement system utilizing electrolytic light emission to thus ensure highly sensitive analysis of dioxins, which do not require the use of any reagent such as hydrogen peroxide required for the chemical luminescence, which permits the miniaturization of the device and which can increase the sensitivity of the analysis.

The inventors of this invention have conducted various studies to solve the foregoing problems and as a result, have completed the present invention.

According to a first aspect of the present invention, there is provided a method for determining the concentration of dioxins present in a sample, which comprises the steps of chemically binding a hapten having a structure mimic to a part of the structures of dioxins with a ruthenium complex to thus form an antigen; incubating the resulting antigen together with an antibody fixed to or immobilized on an electrode to thus induce an antigen-antibody reaction; oxidizing or reducing the ruthenium complex by applying an electric voltage to the reaction product through the electrode to thus induce electrolytic light emission; and observing the electrolytically emitted light rays to quantitatively determine the amount of the antigen and to thus evaluate the concentration of the dioxins present in the sample.

According to a second aspect of the present invention, there is provided a method for determining the concentration of a dioxin present in a sample, which comprises the steps of providing a first electrode onto which an antibody to the dioxin is immobilized; immersing the first electrode in a first liquid containing the sample and an antigen, said antigen being formed by chemically binding a hapten having a structure mimic to a part of the structure of the dioxin with a ruthenium complex; incubating the liquid together with the first electrode to thus induce a competitive antigen-antibody reaction between the antibody and the antigen (dioxin) and the hapten; taking out the first electrode and washing it to remove the antigen and the hapten that are not reacted with the antibody; immersing the first electrode and a second electrode in a second liquid containing a reducing agent and an electrolyte; applying to the second liquid an electric voltage through the first and the second electrodes to oxidize the ruthenium complex; allowing the oxidized ruthenium complex to be reduced by the reducing agent to thus induce electrolytic light emission; detecting the electrolytically emitted light rays; and obtaining the amount of the dioxin present in the sample by the use of a calibration curve.

According to a third aspect of the present invention, there is provided a measuring device used in the foregoing method for determining the concentration of dioxins present in a sample, which comprises a measurement liquid prepared by dissolving a ruthenium complex and trimethylamine in a phosphate-buffered aqueous solution; a gold electrode through which an electric voltage is applied to the liquid; an antibody fixed to or immobilized on the gold electrode; an emitted light-detector for determining the intensity of the electrolytically emitted light rays; and an arithmetic unit for quantitatively determining the concentration of the dioxins present in the sample based on the intensity of the emitted light detected by the emitted light-detector.

BRIEF DESCRIPTION OF THE DRAWINGS

The present invention will hereunder be described in more detail with reference to the figures attached hereto, wherein.

DESCRIPTION OF THE PREFERRED EMBODIMENTS

Regarding the functions of the dioxins, it has been known that if a chemical substance (such as dioxin, dibenzofuran and coplanar PCB) having a planar structure is incorporated into cells, the substance shows a high affinity for a protein called Ah receptor and links therewith. Therefore, the present invention makes the best use of such properties of the dioxin. More specifically, the present invention first forms a foreign low molecular weight substance whose structure is mimic to only a part of the structure of dioxin and makes the full use of the characteristic properties of the low molecule as a hapten, which can form a specific antigen when the molecule is bonded to a polymer. Then the hapten mimic to only a part of the structure of dioxin is chemically linked with a ruthenium complex to thus form an antigen. The antigen can initiate an electrolytic light-emitting reaction simply by the oxidation-reduction. The resulting antigen is incubated along with an antibody immobilized on an electrode to thus induce an antigen-antibody reaction. An electric voltage is applied to the reaction product through the electrodes to induce electrolytic light emission. Then the antigen can be quantitatively analyzed by the observation of the intensity of the emitted light rays to thus determine the concentration of dioxins. Thus, the present invention permits the analysis of dioxins present in a sample without using any reagent required for the chemical luminescence such as hydrogen peroxide, permits the miniaturization of a measuring device to be used in this analysis and also permits the improvement of the sensitivity of the analysis.

Figure 1:
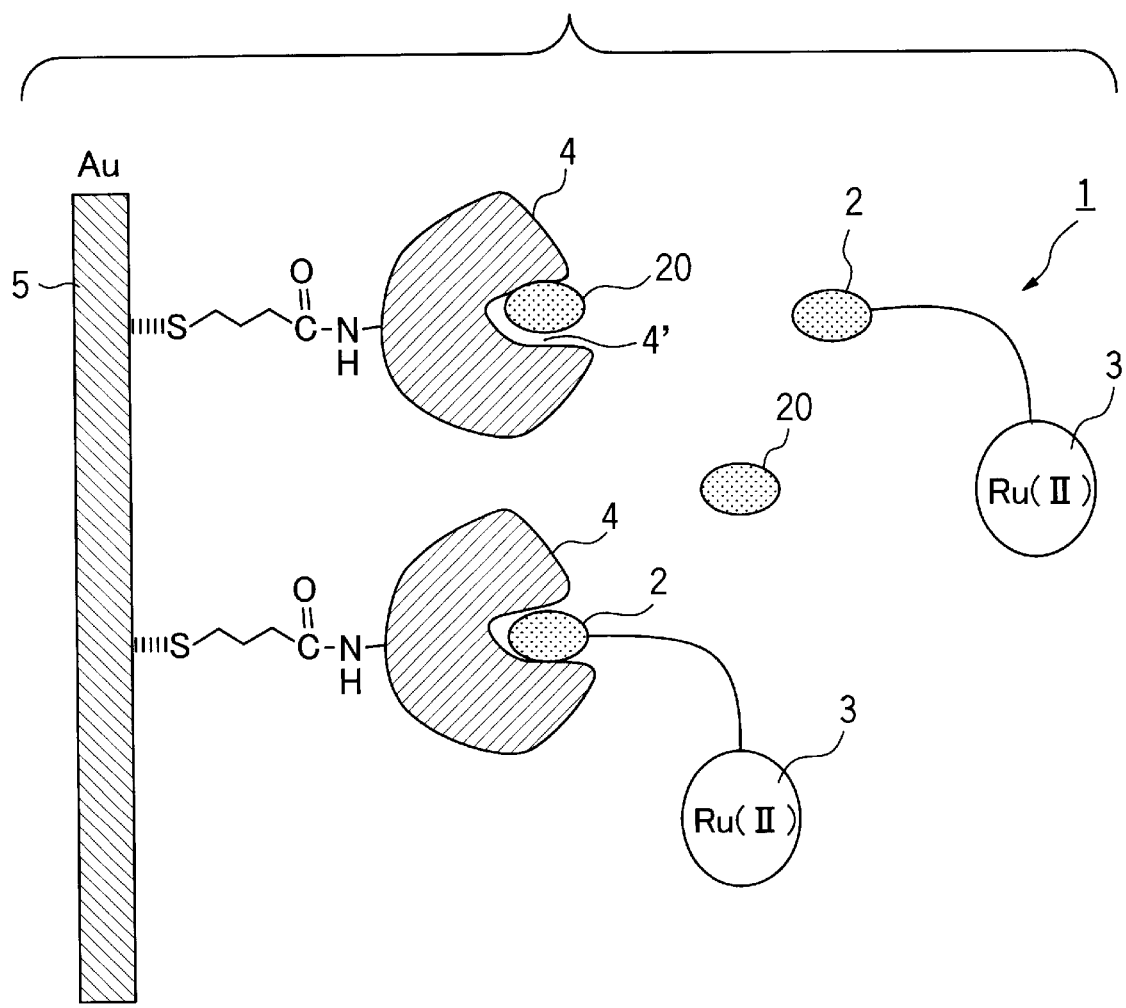
FIG. 1 is a schematic diagram illustrating the situation in which dioxin and the dioxin hapten site of an electrolytically light-emitting reagent are competitively linked with a dioxin antibody.

We will hereunder explain the formation of an antigen 1 (see FIG. 1) serving as an electrolytically light-emitting reagent through the chemical linkage of a dioxin-hapten site 2 (see FIG. 1) with a ruthenium complex 3 (see FIG. 1). First, the dioxin-hapten can be prepared according to, for instance, the following reaction scheme (1):

[Reaction Scheme 1]

The compound (A) in the left side of the chemical scheme is, for instance, a phthalic acid ester: 4,5-dichlorophthalic acid anhydride having a part of the structure of 2,3-dibenzodioxin. This compound (A) is reacted with a compound (B): 4-(p-aminophenyl) butanoic acid serving as a spacer when the hapten is linked with an antibody to thus form a compound (C): N-(4',5'-dichlorophthaloyl)-4-(-p-aminophenyl) butanoic acid. In this respect, the portion (C) is the hapten site and this is linked with a ruthenium complex through the carboxyl group present on the portion (D).

On the other hand, it is also necessary to add a reagent, which can serve as a spacer when the resulting antigen is linked with the antibody, to the ruthenium complex 3. The preparation of such a ruthenium complex 3 will be detailed below with reference to the following reaction schemes (2) to (6):

[Reaction Scheme 2]

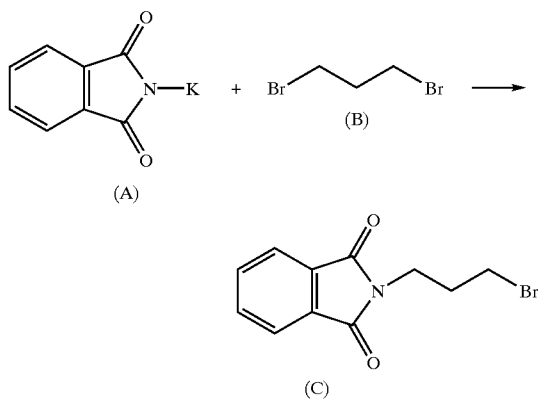

According to the reaction scheme (2), potassium phthalimide (A) is reacted with 1,3-dibromopropane (B) to give 1-(N-phthaloylamino)-3-bromopropane (C) serving as a spacer when the resulting antigen is linked with an antibody.

[Reaction Scheme 3]

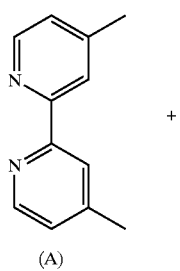

Then, according to the reaction scheme 3, 4,4'-dimethyl-2,2'-bipyridine (A) is reacted with 1-(N-phthaloylamino)-3-bromopropane (B) prepared according to the reaction scheme 2 to give 4-(4-N-phthaloylamino) butyl)-4'-methyl-2,2'-bipyridine (C).

[Reaction Scheme 4]

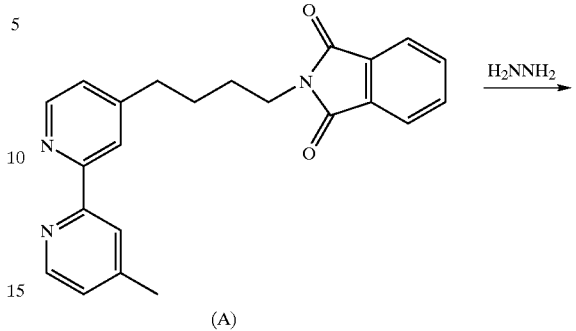

Moreover, 4-(4-(N-phthaloylamino) butyl)-4'-methyl-2,2'-bipyridine (A) is reduced with hydrazine $H_2NNH_2$ to give 4-(4-aminobutyl)-4'-methyl-2,2'-bipyridine (B) according to the reaction scheme 4.

[Reaction Scheme 5]

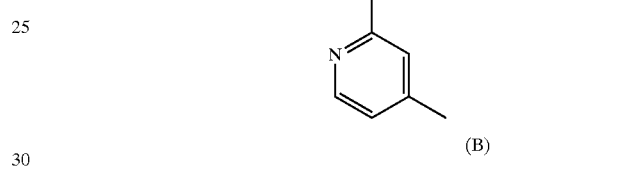

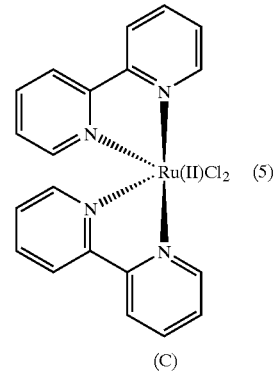

Then 2,2'-bipyridine (A) is reacted with ruthenium trichloride to give dichlorobis (2,2'-bipyridine) ruthenium (C), according to the reaction scheme 5.

[Reaction Scheme 6]

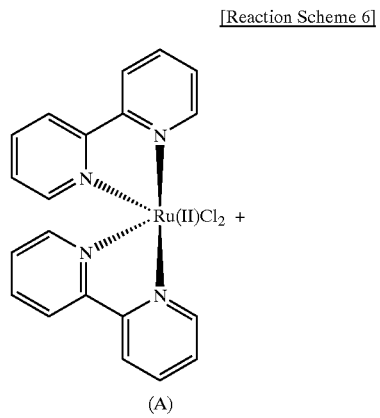

(A)

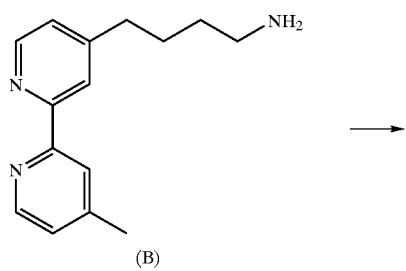

(B)

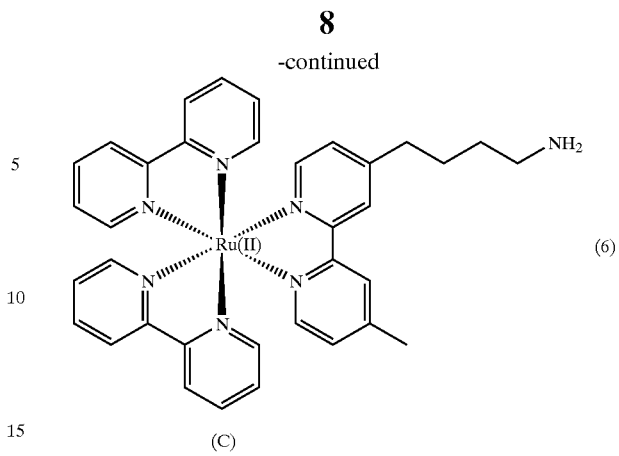

(C)

According to the reaction scheme 6, dichlorobis (2,2'-bipyridine) ruthenium (A) prepared in the reaction scheme 5 is reacted with 4-(4-aminobutyl)-4'-methyl-2,2'-bipyridine (B) prepared in the reaction scheme 4 to thus finally form bis (2,2'-bipyridyl) [4-(4-aminobutyl)-4'-methyl-2,2'-bipyiidine] ruthenium complex (C) carrying a spacer utilized when the hapten is linked with an antibody.

Subsequently, N-(4',5'-dichlorophthaloyl)-4-(p-aminophenyl) butanoic acid of the reaction scheme 1 having a spacer is reacted with bis (2,2'-bipyridyl) [4-(4-aminobutyl)-4'-methyl-2,2'-bipyridine] ruthenium complex of the reaction scheme 6 likewise having a spacer to thus give the antigen 1 serving as an electrolytically light-emitting reagent, which comprises a hapten of dioxins chemically linked with a ruthenium complex.

[Reaction Scheme 7]

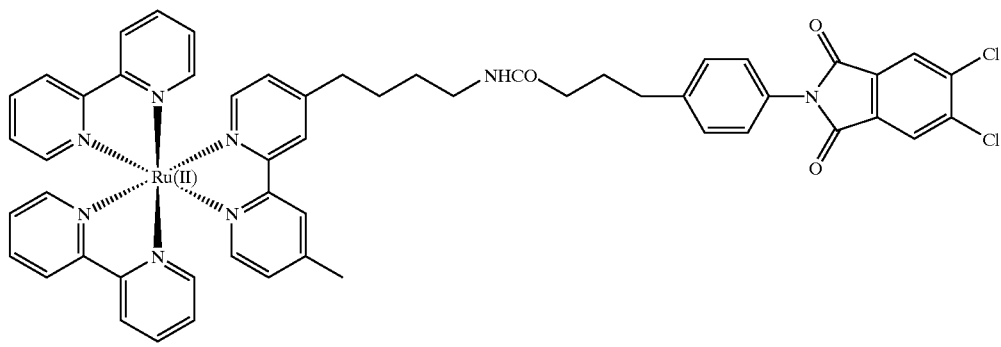

At this stage, if the amount of the [4-(4-aminobutyl)-4'-methyl-2,2'-bipyridine] ruthenium complex can quantitatively be determined, the hapten sites of dioxins can likewise be quantitatively determined.

FIG. 1 is a schematic diagram illustrating the situation in which dioxin 20 and the dioxins-hapten site 2 of an antigen 1 comprising a ruthenium complex 3 linked thereto are competitively linked with a dioxin antibody 4. The antigen-antibody reaction involved in the quantitative analysis of the present invention will hereunder be described in more detail with reference to FIG. 1. The dioxin hapten 2 whose structure is mimic to a part of the structures of dioxins 20 is chemically linked with a ruthenium complex 3 to form an antigen 1 (see the foregoing reaction schemes 1 to 7) and the resulting antigen 1 thus serves as an electrolytically light-emitting reagent. The antigen 1 and the dioxins 20 are incubated along with an antibody 4 immobilized onto the surface of an electrode 5 to thus induce an antigen-antibody reaction. In this respect, however, any chemical bond is not involved in this antigen-antibody reaction, but the reaction is taken place through weak interaction therebetween including, for instance, hydrogen bonds. There are a large number of sites, involved in such interaction, on the antibody 4 and therefore, the antibody 4 has a high ability of recognizing the dioxin hapten site 2 and the dioxins 20 and accordingly, it is strongly linked with the hapten site 2 and the dioxins 20. This would be imagined such that the antibody 4 includes a gap 4' having a shape similar to that of the dioxin hapten site 2 and the dioxins 20 and the latter are completely accommodated in the gap as will be seen from FIG. 1.

Then, the mechanism of the antigen-antibody reaction will be detailed below. First, the antibody 4 is immobilized onto the surface of a gold electrode 5 through a chemical bond. More specifically, the gold electrode 5 is treated with an acid such as sulfuric acid to thus make the surface thereof clean and the electrode 5 is then dipped in a solution of 3,3'-dithiodipropanoic acid ($HOOCCH_2CH_2S—SCH_2CH_2COOH$) (10 mM) for 30 minutes to thus chemically adsorb the 3,3'-dithiodipropanoic acid molecules on the surface of the gold electrode 5 (the chemical bond formed through the interaction between the sulfur atom (S) on the 3,3'-dithiodipropanoic acid and the gold atom (Au) constructing the electrode 5). Then the gold electrode 5 is taken out from the solution and washed with an alcohol such as methanol. Moreover, the gold electrode 5 is additionally dipped in 20 ml of a 90% aqueous dioxane solution supplemented with 30 mg of hydroxy succinimide and 50 mg of a water-soluble carbodiimide (1-ethyl-3-dimethylaminopropyl carbodiimide hydrochloride) for 15 minutes in order to activate the carboxyl group of the 3,3'-dithiodipropanoic acid immobilized onto the surface of the gold electrode 5. Thereafter, the gold electrode 5 carrying the activated 3,3'-dithiodipropanoic acid molecules is immersed in a solution containing the antibody 4 at room temperature for 1 to 10 minutes to thus form amido bonds (—CONH—) through the reaction between amino groups ($NH_2$—) of the antibody 4 and the carboxyl groups of the 3,3'-dithiodipropanoic acid molecules. Thus, the antibody 4 is firmly immobilized onto the gold electrode 5. Subsequently, the gold electrode 5 is washed with a phosphate buffer to remove the antibody 4 molecules which are not chemically bonded with the electrode 5 through the spacers.

On the other hand, a predetermined amount of the antigen 1 obtained by chemically linking the dioxin hapten site 2 and the ruthenium complex 3 is added to a measurement liquid prepared from a phosphate buffer supplemented with 3% DMSO (dimethylsulfoxide). DMSO is used to fully dissolve the dioxins in the liquid. If a liquid prepared from a 0.2 M phosphate-buffered solution (pH=7.0) containing 3% DMSO is used as a sample to be analyzed or only a small amount of DMSO is added to a sample, dioxins can be dissolved in the sample solution to a level on the order of ppb. Then the gold electrode 5 on which the antibody 4 is immobilized is dipped in this measurement liquid, followed by the incubation thereof for 10 minutes to cause an antigen-antibody reaction. Thereafter, the gold electrode 5 is removed from the measurement liquid and then lightly washed with a phosphate buffer (pH 7.0).

Figure 2:
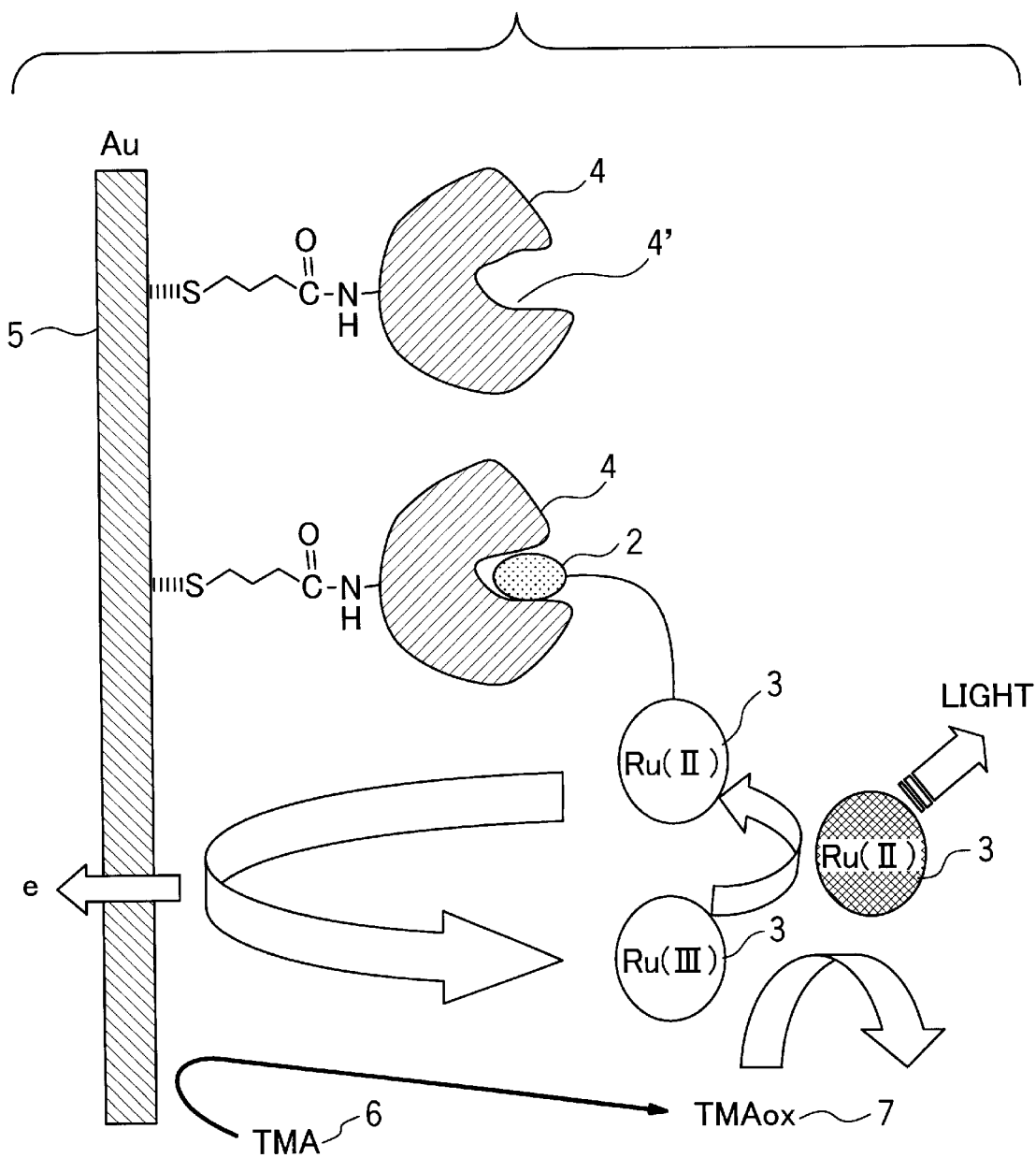
FIG. 2 is a schematic diagram showing how to electrolytically emit light at the hapten site.

FIG. 2 is a schematic diagram showing the mechanism of electrolytic light emission by the antigen 1 formed from chemically linked dioxin hapten site 2 and the ruthenium complex 3. As will be seen from FIG. 2, the electrode 5 (anode), a cathode such as a stainless steel electrode (not shown) and a reference electrode such as silver/silver chloride electrode (not shown) are immersed in a phosphate buffer containing a reducing agent such as a tertiary lower alkyl amine such as trimethylamine (TMA), triethylamine, tripropylamine, tributylamine, an amino acid such as proline, or an organic acid such as oxalic acid. An electric voltage (0.9 to 1.3V) is applied to the electrode 5 at a temperature of 15 to 30° C. for 20 seconds to 2 minutes to induce electrolytic light emission and the intensity of the electrolytically emitted light rays is then determined.

Figure 4:
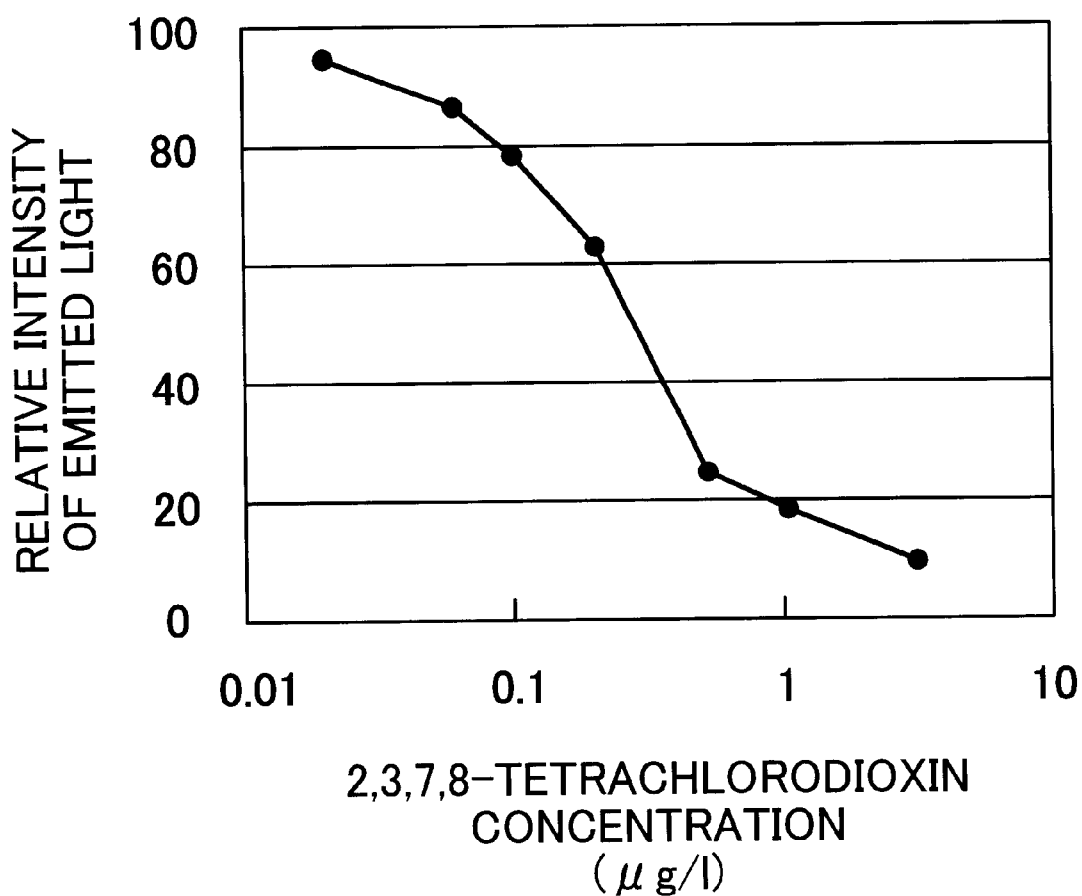
FIG. 4 is a graph (a calibration curve) showing the correlation between the concentration of dioxins and the intensity of the emitted light.

The above procedures are conducted with respect to several samples containing a dioxin in several concentrations and the antigen 1 in a given concentration for example 20 μg/L. The data are plotted to prepare a calibration curve as shown in FIG. 4.

The materials required for the foregoing electrolytic light emission are a ruthenium complex 3 and a phosphate buffer containing a reducing agent such as trimethylamine (TMA) 6. The gold electrode 5 oxidizes the ruthenium complex 3 or the valency of the complex 3 (or ruthenium) is changed from 2 to 3 and thus the complex is converted into an activated reagent. The activated complex 3 is then reacted with trimethylamine (TMA) 6 that is oxidized to give TMAox 7 (an oxidation product of TMA) or TMA reduces the activated complex (the valency thereof is reduced from 3 to 2) to thus emit light rays. The phosphate buffer is important for optimizing the conditions for the light emission. More specifically, the buffer serves as an electrolyte or can ensure conductivity required for the electrolysis and can control the pH value (pH 7.0) of the environment for the electrolysis. The ruthenium complex 3 is bonded to the antibody 4 immobilized onto the surface of the gold electrode 5 in inverse proportion to the dioxin concentration of the aqueous solution, but the amount of the ruthenium complex linked to the antibody is reduced when the dioxin concentration of the aqueous solution is high. Thereafter, the gold electrode 5 carrying the ruthenium complex 3 linked therewith is lightly washed to eliminate the influence of any inhibitory substance present in the dioxin solution to an extent as low as possible and introduced into an aqueous phosphate-buffered solution containing trimethylamine (TMA) 6 separately prepared. Then the electrolytically emitted light is observed or quantified.

Figure 3:
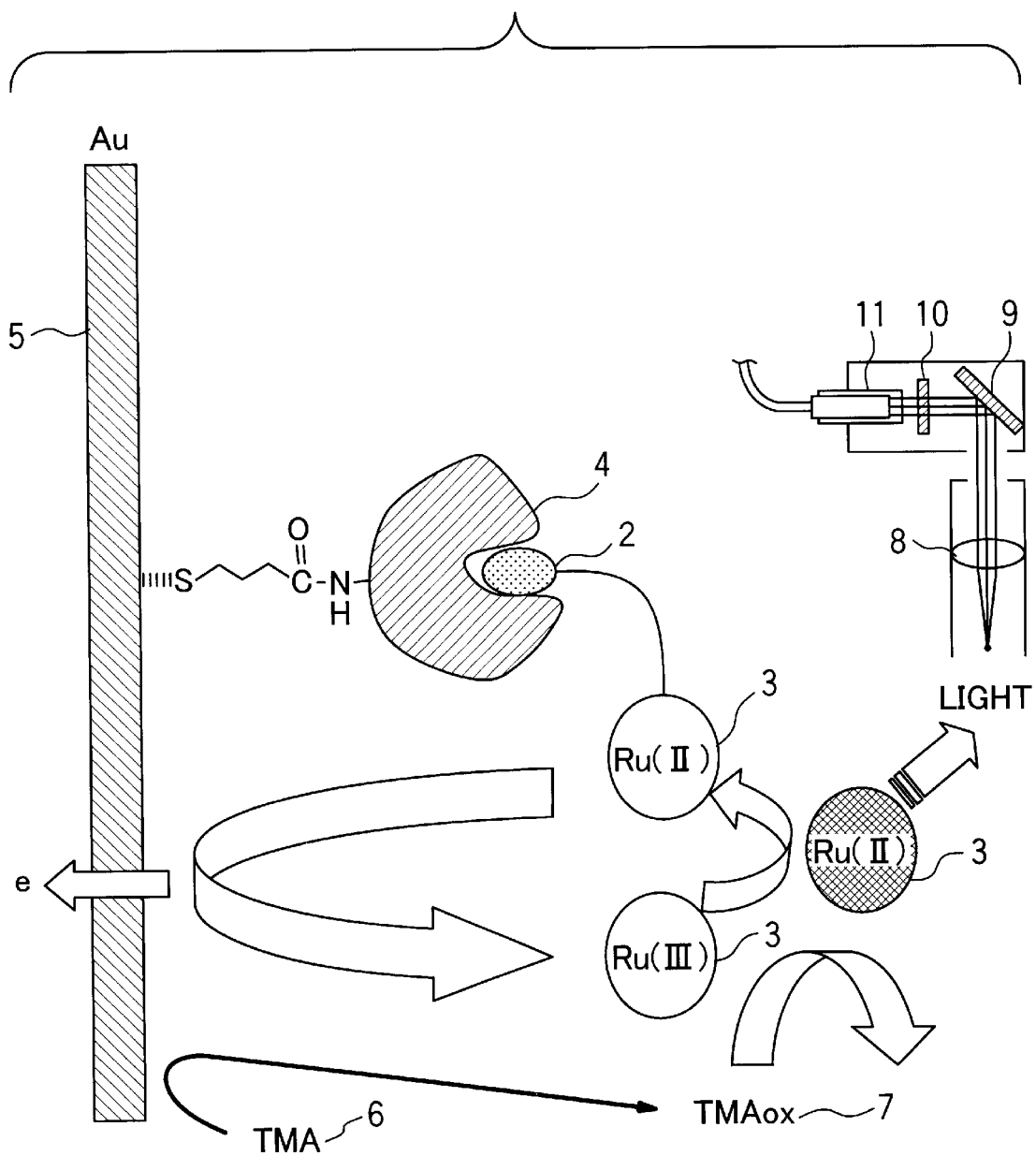
FIG. 3 is a schematic diagram showing a detection device for the observation of electrolytically emitted light rays.

The electrolytically emitted light is preferably detected using a detection device such as that shown in FIG. 3, which comprises a condenser lens 8, a mirror 9, an optical filter 10 and a detection sensor 11. The amount of the ruthenium complex present in a sample can quantitatively be determined by monitoring the intensity of emitted light and the light-emitting duration detected by the detection sensor 11. Moreover, the relation between the amounts of the ruthenium complex and the dioxin hapten site has been determined in advance and therefore, the amount of dioxin present in the sample can quantitatively be determined. In this connection, it is desirable to use an arithmetic unit (not shown) such as a personal computer so that a calibration curve such as that shown in FIG. 4 is inputted into the memory thereof in advance to thus permit the quantitative determination of the amount of the dioxin present in the sample based on the intensity of the emitted light.

As seen from the explanation above, according to the present invention, a sample containing dioxins is added to a first liquid containing a given amount of the antigen 1. In the liquid, the electrode (anode) 5 onto which the antibody 4 is immobilized is immersed to cause an antigen-antibody reaction between the antibody 4 immobilized onto the electrode 5 and the antigen 1 and dioxins 20. That is, the dioxins in the sample and the antigen 1 competitively react with the antibody 4. If the concentration of the dioxins in the sample is high, the reaction ratio of the dioxins to the antibody 4 is high, while the reaction ratio of the antigen 1 to the antibody 4 is low. As a result, the intensity of emitted light is low. On the other hand, if the concentration of the dioxins in the sample is low, the reaction ratio of the dioxins to the antibody 4 is low, while the reaction ratio of the antigen 1 to the antibody 4 is high.

Then, the electrode (anode) 5 onto which the antibody 4 is immobilized, the antibody 4 being linked with the antigen 1 or the dioxins in the sample, is immersed in a second liquid containing a reducing agent and an electrolyte such as a phosphate buffer. A cathode such as a stainless steel cathode and a reference electrode such as Ag/AgCl are also immersed in the second liquid. An electric voltage is then applied to the second liquid through the electrodes to oxidize the ruthenium complex 3. The oxidized ruthenium complex 3 is then reduced by the reducing agent to emit a light. The emitted light is detected by the detector. The intensity of emitted light is in proportion to the amount of the ruthenium complex 3. Thus, if the intensity of the emitted light is detected, the concentration of the dioxins in the sample can be obtained from the calibration curve prepared in advance.

The present invention will hereunder be described in more detail with reference to the following working Example, but the present invention is not restricted to the specific Example at all.

EXAMPLE

As an example of the present invention, the correlation between the dioxin concentration and the intensity of emitted light (calibration curve) was determined.

A liquid containing 2,3,7,8-tetrachloro-p-dibenzodioxin in the concentration of 0.02, 0.06, 0.1, 0.2, 0.5, 1.0 or 3.0 $\mu$g/L in a 0.2 M phosphate buffer containing 3% DMSO (dimethylsulfoxide) was prepared. To the liquid, the antigen 1 prepared according to the method mentioned above and trimethylamine were added in the concentration of 20$\mu$g/L and 1 mol/L, respectively.

The gold electrode 5 (anode) onto which the antibody (EWVATITGGGTYTYYPDSVRGC) had been immobilized and which was prepared according to the method mentioned above, a stainless steel electrode (cathode) and a reference electrode (silver/silver chloride) were immersed in the liquid containing the antigen and incubated at room temperature for 2 minutes. The electric voltage of 1.1V was applied to the electrodes at room temperature for 1 minutes and the emitted light was detected by the detection device as shown in FIG. 3.

The results thus observed are plotted on FIG. 4 as a graph. The data of FIG. 4 clearly indicate that the intensity of electrolytically emitted light rays can be recognized by the method and device of the present invention even if the dioxin concentration is quite low (for instance, 0.01 to 0.1 ppb) and that the sensitivity of the determination of the dioxin concentration can easily and considerably be improved.

As has been described above in detail, the present invention determines the concentration of dioxins present in a sample, by chemically linking a hapten having a structure mimic to a part of the structures of dioxins with a ruthenium complex to thus form an antigen; incubating the resulting antigen together with an antibody fixed to or immobilized on an electrode to thus induce an antigen-antibody reaction; oxidizing or reducing the ruthenium complex by applying an electric voltage to the reaction product through the electrode to thus induce electrolytic light emission; and observing the electrolytically emitted light rays to quantitatively determine the amount of the antigen and to thus evaluate the concentration of the dioxins present in the sample. Accordingly, the present invention does not require the use of any reagent such as hydrogen peroxide required for the chemical luminescence, the present invention can ensure highly sensitive analysis of dioxins and the present invention permits the miniaturization of the device to be used in the analysis of dioxins.

What is claimed is:

1. A method for determining the concentration of dioxins present in a sample, comprising the steps of:

chemically linking a hapten having a 4,5-dichlorophthaloyl group with a ruthenium complex to thus form a hapten/ruthenium complex antigen;

contacting the sample containing the dioxins with an antibody fixed to or immobilized on an electrode and the hapten/ruthenium complex antigen;

allowing the dioxins contained in the sample to compete with the hapten/ruthenium complex antigen to thus form an antigen-antibody reaction product;

applying an electric voltage to the reaction product through the electrode to oxidize or reduce the ruthenium complex thereby induce electrolytic light emission; and observing the electrolytically emitted light rays to quantitatively determine the amount of the antigen and to thus evaluate the concentration of the dioxins present in the sample.

2. The method of claim 1, wherein the electrolytic light emission of the ruthenium complex makes use of an oxidation reaction in which the complex or ruthenium receives an electric charge or the valency thereof is changed from 2 to 3 and a reduction reaction with a phosphate-buffered solution containing trimethylamine in which the valency is reduced from 3 to 2.

3. The method of claim 1 or 2, wherein the antigen is incubated along with the antibody immobilized onto the electrode in a phosphate buffer containing 3% dimethylsulfoxide to thus cause an antigen-antibody reaction.

4. The method of claim 1, wherein the hapten/ruthenium complex antigen is represented by the formula:

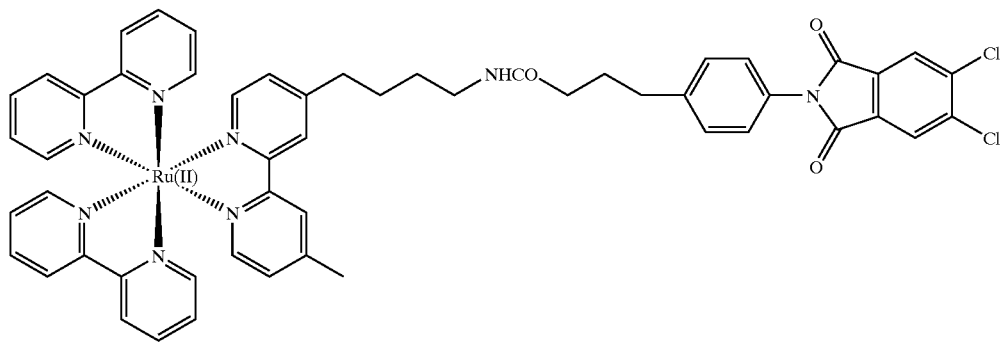
5. The method of claim 1, wherein the dioxins are polychlorinated dibenzo-p-dioxins.
6. The method of claim 1, wherein the dioxins are 2,3,7,8-tetrachloro-dibenzo-p-dioxin.
* * * * *